United States Patent
Langhals et al.

[11] Patent Number: 6,143,890
[45] Date of Patent: Nov. 7, 2000

[54] NAPHTHALENEHYDRAZAMIMIDES AND PERYLENEHYDRAZAMIMIDES

[75] Inventors: Heinz Langhals, Ottobrunn; Rami Ismael, München, both of Germany

[73] Assignee: Ciba Specialty Chemicals Corporation, Tarrytown, N.Y.

[21] Appl. No.: 09/465,869

[22] Filed: Dec. 16, 1999

[30] Foreign Application Priority Data

Jan. 4, 1999 [DE] Germany .................. 199 00 063

[51] Int. Cl.[7] .................. C07D 471/04; C09B 57/08; C09B 57/12; C09B 5/62
[52] U.S. Cl. ............................ 544/233; 544/234
[58] Field of Search ..................... 544/233, 234

[56] References Cited

U.S. PATENT DOCUMENTS

| | | | |
|---|---|---|---|
| 2,992,220 | 7/1961 | Irving et al. ............... | 544/233 |
| 5,319,083 | 6/1994 | Troster ...................... | 546/37 |
| 5,886,183 | 3/1999 | Langhals et al. ........... | 546/62 |
| 5,900,490 | 5/1999 | Feiler ........................ | 549/232 |

FOREIGN PATENT DOCUMENTS 0 896 964   2/1999   European Pat. Off. .

OTHER PUBLICATIONS

L. Chaker et al., Synthesis of 2H–Benzo [2,3–g] pyridazino–[4,5–d,e]quinolin–3–one Derivatives, vo. 128, pp. 681–685(1997).

Z. Kristogr. NCS vol. 214 (1999) pp. 35–37.

Abst. p. of EP 0 896 964, Feb. 17, 1999.

*Primary Examiner*—Fiona T. Powers
*Attorney, Agent, or Firm*—David R. Crichton

[57] ABSTRACT

Hydrazam imides of the general formula I

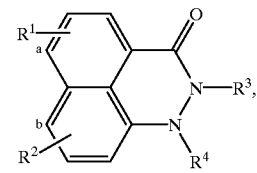

wherein $R^1$ and $R^2$ are each independently of the other (a) hydrogen or nitro, at least one of which radicals being nitro, or $R^1$ and $R^2$ together are (b) one of the following radicals

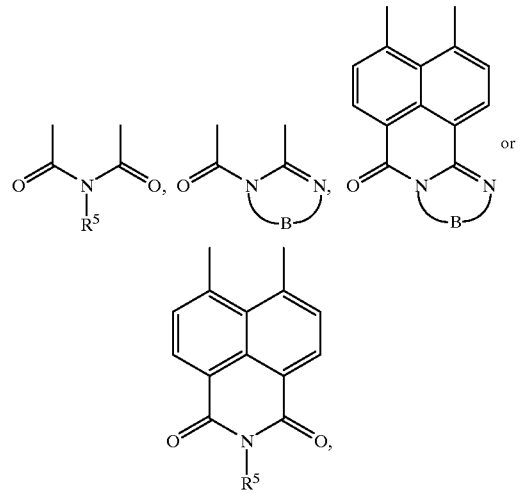

wherein B is

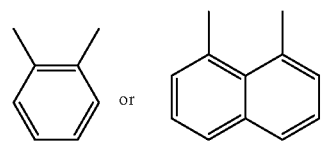

and $R^5$ is $C_1$–$C_{18}$alkyl or $R^3$ or $R^4$, in which case $R^1$ and $R^2$ are bound to the compound of formula I in the positions a and b,
$R^3$ and $R^4$ are each independently of the other unbranched $C_1$–$C_{10}$alkyl, and processes for their preparation and their use.

3 Claims, No Drawings

NAPHTHALENEHYDRAZAMIMIDES AND PERYLENEHYDRAZAMIMIDES

The present invention relates to hydrazamimides of the general formula I

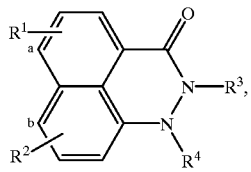

wherein $R^1$ and $R^2$ are each independently of the other (a) hydrogen or nitro, at least one of which radicals being nitro, or $R^1$ and $R^2$ together are (b) one of the following radicals

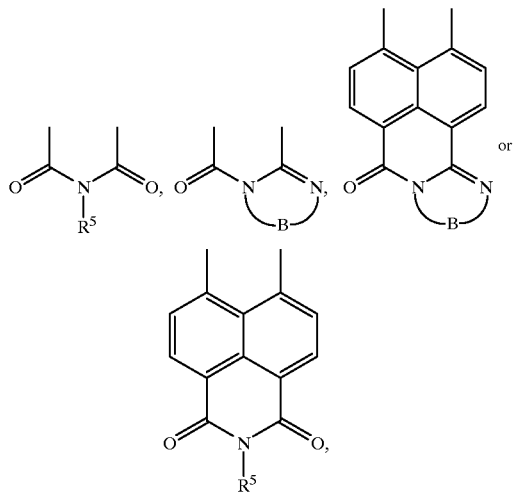

wherein B is

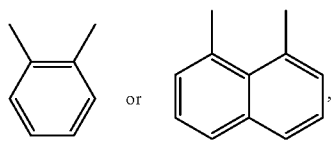

and $R^5$ is $C_1$–$C_{18}$alkyl or $R^3$ or $R^4$, in which case $R^1$ and $R^2$ are bound to the compound of formula I in the positions a and b,
$R^3$ and $R^4$ are each independently of the other unbranched $C_1$–$C_{10}$alkyl. This invention also relates to a process for their preparation and use.

The reaction of perylene-3,4:9,10-tetracarboxylic bisanhydrides ("perylene anhydrides") or naphthalenetetracarboxylic bisanhydrides with primary amines to perylenetetracarboxylic bisimides or naphthalenetetracarboxylic bisimides ("naphthalene anhydrides") is known. The disadvantage of the known bisimides is that their colour intensity and lightfastness is insufficient for some applications and that their UV/vis-absorptions are too hypsochromic.

EP-A 896,964 also discloses the reaction of perylene anhydride imides with hydrazine to form perylene hydrazide imides

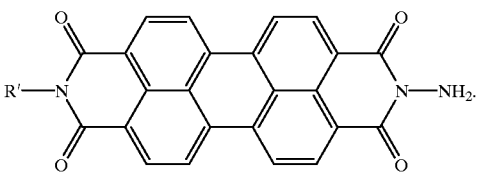

However, the reaction of perylene anhydrides or naphthalene anhydrides with 1,2-disubstituted hydrazines has been unknown so far. The reason for this could be that the reaction products II

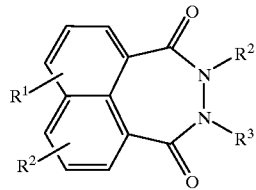

to be expected, which are analogous to I, would contain taut seven-membered rings, which is likely to result in a destabilisation of the products.

Accordingly, this invention has for its object to provide further perylene and naphthalenetetracarboxylic acid derivatives, in particular hydrazamimides, which may be used as pigments or fluorescent dyes. Compared to the known bisimides, the novel colourants should, in particular, have a marked bathochromic shift of the UV/vis-absorption. Blue and violet perylenehydrazamimides should particularly preferably also be provided.

Accordingly, the hydrazamimides I defined at the outset have been found. Processes for their preparation and use were also found.

Unbranched $C_1$–$C_{10}$alkyl is methyl, ethyl, n-propyl, n-butyl, n-pentyl, n-hexyl, n-heptyl, n-octyl, n-nonyl or n-decyl, preferably methyl and n-nonyl.

$C_1$–$C_{18}$Alkyl is, for example, methyl, ethyl, n-propyl, isopropyl, n-butyl, i-butyl, sec-butyl, tert-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl and 1-methylethyl, 1-ethyl-n-propyl, 1-n-propyl-n-butyl, 1-n-butyl-n-pentyl, 1-n-hexyl-1-heptyl, 1-n-heptyl-1-n-octyl, 1-n-octyl-1-n-nonyl, 1-n-nonyl-1-decyl, preferably $C_1$–$C_{14}$alkyl, such as methyl, ethyl, n-propyl, isopropyl, n-butyl, sec-butyl, tert-butyl, tert-amyl, n-hexyl, n-heptyl, n-octyl, n-nonyl, n-decyl, n-undecyl, n-dodecyl, n-tridecyl, 1-n-hexyl-1-heptyl, n-tetradecyl, 3-pentyl, 4-heptyl, 5-nonyl, 6-undecyl, 7-tridecyl, 3-hexyl, 3-heptyl, 3-nonyl, 3-undecyl, particularly preferably $C_1$–$C_8$alkyl, such as methyl, ethyl, n-propyl, isopropyl, n-butyl, i-butyl, sec-butyl, tert-butyl, tert-amyl, n-hexyl, 1,1,3,3, -tetramethylbutyl, n-heptyl, n-octyl, 3-pentyl, 4-heptyl, 3-hexyl, 3-heptyl, very particularly preferably $C_1$–$C_4$alkyl, such as methyl, ethyl, n-propyl, isopropyl, n-butyl, i-butyl, sec-butyl, tert-butyl.

Particularly preferred hydrazamimides I are naphthalenehydrazamimides of formula Ia

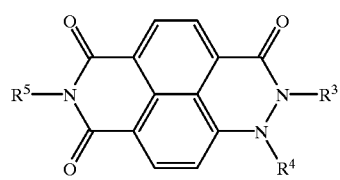

and of formula Ib and Ic

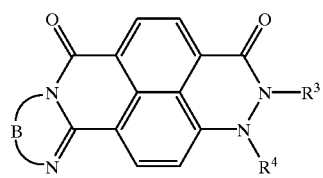

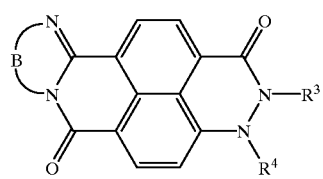

and perylenehydrazamimides of formula Id

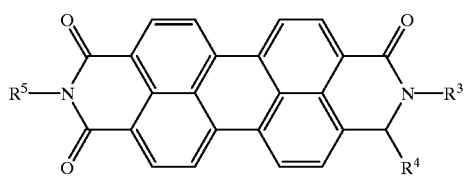

and of formulae Ie and If

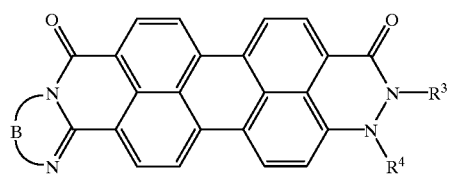

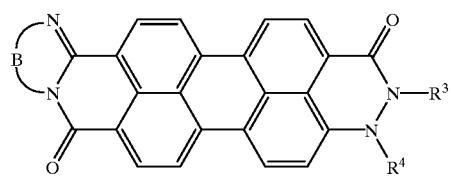

The novel hydrazamimides I are usually obtained by reacting the corresponding anhydrides III

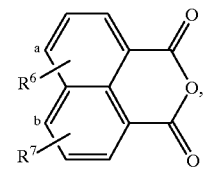

wherein $R^6$ and $R^7$ are each independently of the other (a) hydrogen or nitro, at least one of which radicals being nitro, or $R^6$ and $R^7$ together are (b)

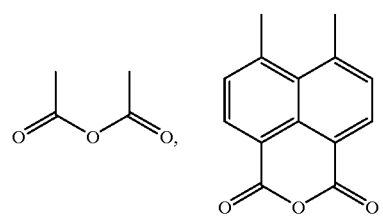

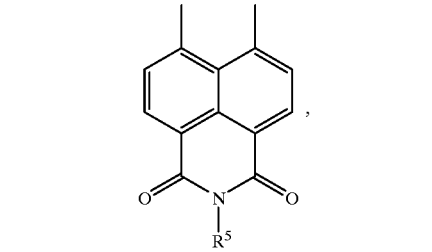

in which case $R^6$ and $R^7$ are bound to the compound of formula III in the positions a and b, with a disubstituted hydrazine, $R^3NHNHR^4$.

This invention therefore also relates to a process for the preparation of the novel hydrazamides I by reacting the anhydride III with the disubstituted hydrazine derivative $R^3NHNHR^4$ at elevated temperature.

The anhydrides III and the hydrazine derivatives are known or are accessible by known methods. It is also possible to replace the hydrazine derivatives with their salt adducts, for example with hydrogen chloride.

Preferred hydrazine derivatives are those, wherein $R^3=R^4$, and particularly preferred are di-methylhydrazine, diethylhydrazine, di-n-propylhydrazine, di-n-butylhydrazine, di-n-pentyhydrazine, di-n-hexylhydrazine, di-n-heptylhydrazine, di-n-octylhydrazine or di-n-nonyhydrazine.

The reaction is preferably carried out in a solvent, such as a basic organic solvent, for example imidazole, quinoline, pyridine, picoline, preferably imidazole.

It is moreover preferred to carry out the reaction in an inert gas atmosphere. Suitable protective gases are, for example, nitrogen and noble gases, such as helium or argon.

The reaction is usually carried out at a temperature in the range from 80 to 200° C., preferably from 125 to 165° C. According to findings so far, the success of the reaction does not depend on the choice of the pressure range. For the sake of simplicity, the reaction is usually carried out at atmospheric pressure, but it is also possible to choose lower pressures of up to 10 kPa or pressures of up to 10 MPa. Depending on the chosen reaction temperature and the reactivity of the educts, the reaction times are chosen e.g. to be preferably in the range from one hour to five hours if the reaction is carried out in the preferred temperature range.

The molar ratio of disubstituted hydrazine to anhydride III is usually chosen to be in the range from 1:1 to 10:1, preferably from 1.5:1 to 6:1.

The weight ratio of solvent to anhydride III is usually chosen to be in the range from 1:1 to 20:1, preferably from 5:1 to 15:1.

The reaction mixture is usually worked up by known methods, for example by chromatography, precipitation or crystallisation. In a preferred embodiment of this invention, the reaction mixture is first treated with an acid, such as a mineral acid, preferably hydrochloric acid, and is then filtered and dried, and the dried reaction product can then be subjected to chromatography for further purification.

In a preferred embodiment of this invention, the reaction is carried out using a disubstituted hydrazine in the presence of a primary amine, $R^5NH_2$, or of a diamine, $H_2N—B—NH_2$.

The reaction is normally carried out as in the above-described reaction without addition of amines, i.e. the reaction parameters usually correspond to the above reaction parameters.

The molar ratio of primary amine or diamine to anhydride III is usually chosen to be in the range from 1:1 to 5:1.

The primary amines ($C_1$–$C_{18}$alkyl-$NH_2$) and the diamines ortho-phenylenediamine and 1,8-di-aminonaphthalene are known. Besides the cited diamines it is also possible to use their standard derivatives, for example alkyl-substituted derivatives.

Accordingly, this invention also relates to a process for the preparation of the hydrazamimides I by reacting the anhydrides III with a hydrazine derivative $R^3NHNHR^4$ in the presence of a primary amine $R^5NH_2$ or a diamine $H_2N—B—NH_2$ at elevated temperature.

Another embodiment of this invention relates to the use of the novel hydrazamimides I as colourants, in particular as pigments and dyes, in general by methods known per se, preferably (a) for mass colouring polymers, where the polymers can be polyvinyl chloride, cellulose acetate, polycarbonates, polyamides, polyurethanes, polyimides, polybenzimidazoles, melamine resins, silicones, polyesters, polyethers, polystyrene, polymethyl methacrylate, polyethylene, polypropylene, polyvinyl acetate, polyacrylonitrile, polybutadiene, polychlorobutadiene or polyisoprene, or the copolymers of the cited monomers;

(b) as vat dyes or mordant dyes, for example for dyeing natural substances and, in particular, paper, wood, straw, leather, hides or natural fibre materials, such as cotton, wool, silk, jute, sisal, hemp, flax or animal hair (e.g. horsehair) and the conversion products thereof, such as viscose fibre, nitrate silk or cuprammonium rayon (rayon), preferred salts for mordanting being aluminium salts, chromium salts and iron salts;

(c) for the preparation of paints, paint systems, in particular automotive lacquers, coating compositions, paper colours, printing colours, inks, in particular for use in ink-jet printers, preferably in homogeneous solution as a fluorescent ink, and for painting and writing purposes, as well as in electrophotography, e.g. for dry copier systems (Xerox process) and laser printers;

(d) for security marking purposes, such as for cheques, cheque cards, currency notes, coupons, documents, identity papers and the like, where a special unmistakable colour impression is to be achieved;

(e) as an additive to colourants, such as pigments and dyes, where a specific colour shade is to be achieved, particularly luminous shades being preferred;

(f) for marking objects for machine recognition of these objects via the fluorescence, preferably for machine recognition of objects for sorting, e.g. including the recycling of plastics, alphanumerical prints or barcodes being preferably used;

(g) for converting the frequency of light, e.g. for turning short-wave light into long-wave visible light or for doubling or tripling the frequency of laser light in non-linear optics;

(h) for the production of passive display elements for a multitude of display, notice and marking purposes, e.g. passive display elements, notices and traffic signs, such as traffic lights;

(i) as starting material for supraconducting organic materials (via π-π-interaction, the addition of e.g. iodine usually resulting in a intermediary charge delocalisation);

(j) for marking with fluorescence in the solid state;

(k) for decorative and artistic purposes;

(l) for tracer purposes, e.g. in biochemistry, medicine, technology and natural science, where the novel colourants can be linked covalently to the substrates or via secondary valences, such as hydrogen bonds or hydrophobic interactions (adsorption);

(m) as fluorescent dyes in highly sensitive detection processes (see Z. Analyt. Chem. 1985, 320, 361), in particular as fluorescent dyes in scintillators;

(n) as dyes or fluorescent dyes in optical light collection systems, in fluorescence solar collectors (see Nachr. Chem. Tech. Lab. 1980, 28, 716), in fluorescence-activated displays (see Elektronik 1977, 26, 6), in cold light sources used for light-induced polymerisation for the preparation of plastics, for testing materials, for example in the production of semiconductor circuits, for analysing microstructures of integrated semiconductor components, in photoconductors, in photographic processes, in display, illumination or image converter systems, where excitation is effected by electrons, ions or UV radiation, e.g. in fluorescent displays, Braun tubes or in fluorescent lamps, as part of an integrated semiconductor circuit containing dyes as such or in combination with other semiconductors, for example in the form of an epitaxy, in chemiluminescence systems, e.g. in chemiluminescent flashlights, in luminescence immunoassays or other luminescence detection processes, as signal paints, preferably for visually emphasising strokes of writing and drawings or other graphic products, for marking signs and other objects for which a particular visual colour impression is to be achieved, in dye lasers, preferably as fluorescent dyes for generating laser beams, as Q-switches, for spectral holeburning, in zeolite cages, in protein-colourant combinations, in antibody-colourant combinations, for colouring DNA or RNA, and in fluorescence quantum counters;

(o) as rheology improvers, and (p) for use in single-molecule-speltroscopy.

Compared to the corresponding bisimides, the novel compounds have a substantial bathochromic shift of the UV/vis-absorption. For example, in contrast to the almost colourless naphthalenebisimides, the novel naphthalenehydrazamimides form lightfast and intensely red solutions, making these substances interesting for use as colourants. They furthermore have substantial yellow fluorescence. Furthermore, a marked solid-state fluorescence is found in some derivatives. In the case of the perylenehydrazamimides the absorption and fluorescence is even more long-wave than in the case of the corresponding bisimides so that solutions may be obtained which are already blue. The fluorescence of the substances is already so long-wave that a substantial part thereof extends to up the near infrared (NIR) range. As these substances have very high fastness to light, they are of great interest inter alia as NIR fluorescent dyes.

EXAMPLES

Both the synthesis and the purification and working up of the hydrazines are carried out using heated apparatus charged with argon and absolute solvents deaerated with argon.

Example 1

17.8 g (156 mmol) of heptanal are added to 15 g of calcium oxide and this mixture is charged incrementally with 3.9 g (78 mmol) of hydrazine hydrate. The reaction mixture, which becomes highly viscous, is diluted with about 20 ml of absolute ethanol. After refluxing for 2 hours, the solid is collected by filtration and washed with absolute ethanol. The filtrate is concentrated by evaporation in a rotary evaporator to ¼ of the liquid volume. The heptanalazine is then separated by distillation from the unreacted heptanal and from the solvent. Yield: 8.5 g (49%) of a slightly yellow and somewhat viscous liquid, m.p.: 120° C./1.2 mbar.

Example 2

The synthesis is carried out in analogy to Example 1 by condensing nonanal with hydrazine hydrate in ethanol with addition of CaO as desiccant. Batch: 8.32 g (181 mmol) of hydrazine hydrate, 28.3 g (199 mmol) of nonanal. Yield: 27.84 g (55%) of slightly yellow and somewhat viscous liquid. M.p: 154° C./0.46 mbar.

Example 3

8.4 g (40 mmol) of heptanalazine are dissolved under argon in 30 ml of absolute ether which is deaerated with argon. This solution is added dropwise under argon to a suspension consisting of 5.7 g (15 mmol) of lithium aluminium hydride in 150 ml of absolute ether. After refluxing for 1 hour, a dilute hydroxide solution is slowly added, with cooling with ice, until no evolution of gas ($H_2$) can be found anymore. The mixture is extracted with ether and the organic phase is then removed from the solvent under normal pressure. The mixture is then subjected to distillation under vacuum. After the distillation the apparatus is slowly charged with argon so as to prevent the hydrazines from any contact with air. Yield: 6.02 g (66%), m.p.: 130° C./1.2 mbar.

Example 4

The procedure of Example 3 is repeated using the following substances: 27.7 g (98.0 mmol) of N,N'-dinonylazine, 9.00 g (23.7 mmol) of $LiAlH_4$ in 250 ml absol. ether. Yield: 17.4 g, m.p.: 158° C./0.81 mbar. When left standing, N,N'-dinonylhydrazine crystallises out under argon as colourless platelets.

Example 5

0.83 g (3.1 mmol) of naphthalene-1,8:4,5-tetracarboxylic bisanhydride, 1.55 g (6.79 mmol) of N,N'-diheptylhydrazine and 5 g of imidazole are reacted for 2 hours at 135–150° C. under argon. The cooled mixture is extracted in 300 ml of 2N-HCl to separate excess hydrazine and imidazole. After filtration (over a D4 frit), the residue is dried overnight at 70° C., yielding an orange-red dye mixture which is purified by column chromatography. Using $CHCl_3$/acetone (15:1) as eluant, three main fractions are obtained. After further chromatogrphy using chloroform as eluant, it is possible to identify in the first main fraction minor amounts of N,N'-diheptyl-naphthalene-1,8:4,5-bis(dicarboximide) and minor amounts of N,N'-diheptyl-N"-heptylnaphthalene-1:4,5-tricarboxylic acid-4,5-imide-1,8-hydrazam. N-heptyl-N'-heptylaminonaphthalene-1,8:4:5-bis(dicarboximide) is obtained as main product from this fraction. Yield: 0.13 g (9%) of a yellow powder, m.p. 182° C.—$R_f$(silica gel, chloroform/EtOH 15:1)=0.66.—IR (KBr): ν=3436 $cm^{-1}$ m, 2927 m ($CH_2$), 2856 m ($CH_2$), 1702 m (C=O), 1660 s (C=O), 1582 w, 1453 w, 1374 w, 1344 m, 1246 m, 1183 w, 1093 w, 768 m, 570 w.—UV/vis ($CHCl_3$): $\lambda_{max}$=359,9 nm (19900), 380,4 (22400).

$C_{28}H_{35}N_3O_4$ (477.6): calcd. C, 70.40; H, 7.39; N, 8.80; found C, 70.44; H, 7.37; N, 8.76.

The second fraction is subjected to chromatography with $CHCl_3$/acetone (15:1), yielding N,N'-diheptyl-N"-heptylaminonaphthalene-1:4,5-tricarboxylic acid-4,5-imide-1,8-hydrazam as main product. Yield: 0.24 g (14%) of a red powder, m.p.: 96° C.—$R_f$(silica gel, chloroform/ethanol 10:1)=0.43.—IR (KBr): ν=3436 $cm^{-1}$ w, 2957 s , 2925 s, 2855 s, 1690 m, 1647 s, 1616 m, 1590 s, 1527 w, 1467 w, 1388 w, 1110 w, 752 w.—UV/vis ($CHCl_3$): $\lambda_{max}$= 351 nm (6720), 481.6 (12430).—Fluorescence ($CHCl_3$): $\lambda_{max}$=565 nm, 588.—Fluorescence quantum yield ($CHCl_3$): 20%, based on N,N'-(1-hexylheptyl)-perylene-3,4:9,10-bis-(dicarboximide) with 100% fluorescence quantum yield.—Solid-state fluorescence: $\lambda_{max}$=628 nm.

$C_{34}H_{50}N_4O_3$ (562.8): calcd. C, 72.55; H, 8.96; N, 9.96; found C, 72.38; H, 8.68; N, 9.90.

Subjecting the third fraction to chromatography with $CHCl_3$/acetone (15:1) also yields N,N'-diheptylaminonaphthalene-1,8:4,5-tetracarboxylic acid bisimide. Yield: 0.32 g (21%) of an orange powder, m.p.: 191° C.—$R_f$(silica gel, chloroform/ethanol 10:1)=0.17.—IR (KBr): ν=3430 $cm^{-1}$ w, 3084 w, 2956 m, 2928 m, 2856 m, 1707 s, 1663 s, 1582 m, 1498 w, 1448 w, 1366 w, 1346 m, 1246 s, 1212 w, 1188 m, 1114 w, 1060 w, 1010 w, 980 w, 887 w, 809 w, 728 m, 571 w, 436 w.—UV/vis ($CHCl_3$): $\lambda_{max}$= 359 nm (15020), 380 (14830), 482 (620).

Example 6

The procedure of Example 5 is repeated using the following educts and amounts: 0.83 g (3.1 mmol) of naphthalene-1,8:4,5-tetracarboxylic bisanhydride, 3.18 g (11.2 mmol) of N,N'-dinonylhydrazine and 5 g of imidazole.

$1^{st}$ fraction N-nonyl-N'-nonylaminonaphthalene-1,8:4,5-bis(dicarboximide): Yield: 0.16 g (10%) of a yellow powder, m.p.: 142° C.—$R_f$(silica gel, chloroform/EtOH 10:1)= 0.66.—IR (KBr): ν=3436 $cm^{-1}$ m, 3080 w, 2924 s ($CH_2$), 2854 m ($CH_2$), 1702 s (C=O), 1659 s (C=O), 1582 m, 1453 w, 1374 w, 1345 s, 1246 s, 1215 w, 1192 w, 1179 w, 1123 w, 1097 w, 978 w, 893 w, 767 m, 570 w.

$C_{32}H_{43}N_3O_4$ (533.7): calcd. C, 72.00; H, 8.13; N, 7.88; found C, 72.11; H, 8.40; N, 7.74.

$2^{nd}$ fraction: N,N'-dinonyl-N"-nonylaminonaphthalene-1:4,5-tricarboxylic acid-4,5-imide-1,8-hydrazam: Yield: 0.26 g (13%) of a red powder, m.p.: 88° C.—$R_f$(silica gel, chloroform/ethanol 10:1)=0.46.—IR (KBr): ν=3439 $cm^{-1}$ m, 2957 m, 2920 s, 2851 s, 1690 m, 1647 s, 1616 m, 1595 m, 1531 w, 1467 w, 1402 w, 1385 w, 872 w, 752 m.—UV/vis (CHCl$_3$): $\lambda_{max}$=350 nm (6720), 458.4 sh (8800), 481.6 (12400), 514.0 sh (6700).—Fluorescence (CHCl$_3$): $\lambda_{max}$= 565 nm, 589.—Solid-state fluorescence: $\lambda_{max}$=628 nm.— Fluorescence quantum yield (CHCl$_3$): 20%, based on N,N'-(1-hexylheptyl)-perylene-3,4:9,10-bis(dicarboximide) with 100% fluorescence quantum yield.

C$_{40}$H$_{62}$N$_4$O$_3$ (647.0): calcd. C, 74.25; H, 9.67; N, 8.66; found C, 74.10; H, 9.68; N, 8.40.

3$^{rd}$ fraction: N,N'-bis(nonylamino)-naphthalene-1,8:4,5-bis(dicarboximide): Yield: 0.41 g (24%) of an orange powder, m.p.: 180° C.—R$_f$(silica gel, chloroform/ethanol 10:1)=0.20.—IR (KBr): $\nu$=3435 cm$^{-1}$ m br., 3084 w, 2956 w, 2924 s, 2855 m, 1707 s, 1664 s, 1582 w, 1499 w, 1448 w, 1366 w, 1346 m, 1247 s, 1195 w, 1115 w, 1060 w, 977 w, 888 w, 809 w, 762 m, 724 w, 570 w br.—UV/vis (CHCl$_3$): $\lambda_{max}$=359 nm (15000), 380 (14830), 482 (620).

C$_{32}$H$_{44}$N$_4$O$_4$ (548.7): calcd. C, 70.03; H, 8.09; N, 10.21; found C, 70.03; H, 7.93; N, 10.14.

Example 7 (comparison)

1.0 g (5.4 mmol) of hydrazobenzene, 0.59 g (2.2 mmol) of naphthalene-1,8:4,5-tetracarboxylic bisanhydride and 4 g of imidazole are heated for 2 hours to 135–150° C. After cooling, about 40 ml of ethanol are added to the reaction mixture and then hydrolysis is carried out using a mixture of 100 ml of dilute hydrochloric acid and 200 ml of water. A pale yellow precipitate forms. N,N'-diphenylnaphthalene-1,8:4,5-bis(dicarboximide) is isolated as main product.

Example 8

The procedure of Example 5 is repeated using the following educts and amounts: 300 mg (0.765 mmol) of perylene-3,4:9,10-tetracarboxylic bisanhydride, 0.94 g (4.0 mmol) of N,N'-diheptylhydrazine and 4 g of imidazole.

1$^{st}$ fraction: N,N'-diheptylperylene-3,4:9,10-bis(dicarboximide): Yield: 18 mg (4%), m.p. >320° C.—R$_f$ (silica gel, chloroform)=0.73.—IR (KBr): $\nu$=2955 cm$^{-1}$ m, 2926 s, 2856 m, 1698 s, 1658 s, 1594 s, 1579 m, 1507 w, 1465 w, 1457 w, 1406 m, 1378 w, 1339 s, 1253 m, 1210 w, 1174 m, 1124 w, 1108 w, 960 w, 850 w, 810 m, 795 w, 747 m, 725 w.—UV/vis (CHCl$_3$): $\lambda_{max}$=458 nm (18700), 488 (51400), 525 (80300).—Fluorescence (CHCl$_3$): $\lambda_{max}$=534 nm, 574.

C$_{38}$H$_{38}$N$_2$O$_4$ (586.7): calcd. C, 77.00; H, 6.53; N, 4.78; found C, 76.79; H, 6.48; N, 4.75.

2$^{nd}$ fraction: N-heptylaminoperylene-3,4-dicarboximide: Yield: 18 mg (5.4%), m.p. 263° C.

3$^{rd}$ fraction: 9-heptyl-1,2-dihydro-1,2-diheptylanthraceno[3,4,5-c,d,e]isoquinolino[7,6,5-d,e,f]-cinnoline-3,8,9-trione or N,N'-diheptyl-N"-heptylperylene-3:9,10-tricarboxylic acid-9,10-imide-3,4-hydrazam. Yield: 8 mg (2%), m.p. 218° C.—R$_f$(silica gel, chloroform/ethanol (10:1)=0.56.—IR (KBr): $\nu$=3444 cm$^{-1}$ m, 2958 s, 2927 s, 2857 m, 1684 m, 1644 s, 1611 w, 1575 m, 1505 m, 1462 w, 1398 m, 1391 w, 1351 s, 1288 s, 1259 w, 1220 w, 802 m, 752 w, 731 w.—UV/vis (CHCl$_3$): $\lambda_{max}$=402.4 nm (5041), 591.0 (20177) .—Fluorescence (CHCl$_3$): $\lambda_{max}$=730.9 nm, 815.0 sh.— Fluorescence quantum yield (CHCl$_3$): 7%, based on N,N'-(1-hexyl-heptyl)-perylene-3,4:9,10-bis(dicarboximide) with 100% fluorescence quantum yield.

C$_{44}$H$_{53}$N$_3$O$_3$: calcd. 671.4087; found 671.4082 (MS).— C$_{44}$H$_{53}$N$_3$O$_3$ (671.9): calcd C, 78.64, H, 7.95; N, 6.26; found C, 77.44; H, 7.86; N, 6.31.

4$^{th}$ fraction: N-heptyl-N'-heptylaminoperylene-3,4:9,10-bis(dicarboximide).Yield: 64 mg (14%), m.p.: 311° C.—R$_f$ (silica gel, chloroform/ethanol 10:1)=0.38; UV/vis (CHCl$_3$): $\lambda_{max}$=431.8 nm (4190), 459.0 (18300), 490.0 (50200), 526.7 (82200).—Fluorescence (CHCl$_3$): $\lambda_{max}$=539 nm, 571, 620 sh.

C$_{38}$H$_{39}$N$_3$O$_4$ (601.3): calcd. C, 75.83; H, 6.54; N, 6.99; found C, 75.49; H, 6.28; N, 7.00.

5$^{th}$ fraction: 1,2-diheptyl-9-heptylamino-1,2-dihydroanthraceno[3,4,5-c,d,e]isoquinolino[7,6,5-d,e,f]cinnoline-3,8,9-trione or N,N'-diheptyl-N"-heptylaminoperylene-3:9,10-tricarboxylic acid-9,10-imide-3,4-hydrazam. Yield: 63 mg (12%), m.p.: 198° C.—R$_f$(silica gel, chloroform/ethanol 10:1)=0.17.—IR (KBr): $\nu$=3449 cm$^{-1}$ m, 2956 s, 2924 s, 2854 m, 1684 m, 1646 s, 1610 w, 1574 s, 1505 m, 1461 w, 1390 w, 1352 s, 1290 s, 1258 w, 1221 w, 803 m, 750 w, 729 w.—UV/vis (CHCl$_3$): $\lambda_{max}$=380.4 nm (3200) sh, 402.0 (3700), 603, (18200).—Fluorescence (CHCl$_3$): $\lambda_{max}$=735.6 nm, 819.5 sh.—Fluorescence quantum yield (CHCl$_3$): 10%, based on N,N'-(1-hexylheptyl)-perylene-3,4:9,10-bis(dicarboximide) with 100% fluorescence quantum yield.

C$_{44}$H$_{54}$N$_4$O$_3$ (686.9): calcd. C, 76.92; H, 7.93; N, 8.16; found C, 76.20; H, 8.44; N, 7.67.

6$^{th}$ fraction: N,N'-bis(heptylamino)-perylene-3,4:9,10-bis (dicarboximide). Yield: 132 mg (28%), m.p. >320° C.—R$_f$ (silica gel, chloroform/ethanol 10:1)=0,31.—IR (KBr): $\nu$=3436 cm$^{-1}$ m, 2953 m, 2927 s, 2855 m, 1698 s, 1664 s, 1594 s, 1507 w, 1467 w, 1403 m, 1348 m, 1255 m, 1177 m, 1126 w, 1056 w, 845 w, 808 m, 740 m, 432 w.—UV/vis (CHCl$_3$): $\lambda_{max}$=431.8 nm (4150), 460.2 (18100), 491.0 (50000), 528.3 (81400).—Fluorescence (CHCl$_3$): $\lambda_{max}$=540 nm, 574, 631 sh.

C$_{38}$H$_{40}$N$_4$O$_4$ (616.3): calcd. C, 73.99; H, 6.54; N, 9.09; found C, 73.80; H, 6.91; N, 8.85.

Example 9

59.4 g (0.300 mol) of heptan-4-one are added to 18.6 g of calcium oxide and this mixture is charged incrementally with 4.8 ml (0.10 mol) of hydrazine hydrate. The reaction mixture, which becomes highly viscous, is diluted with about 30 ml of absolute ethanol. After refluxing for 2 hours, the solid is collected by filtration. The solid obtained is washed with absolute ethanol. The filtrate is concentrated by evaporation in a rotary evaporator to ¼of the liquid volume. The N,N'-bis(1-propylbutyl)ketazine is then separated by distillation from the unreacted heptan-4-one and from the solvent. The N,N'-bis(1-propylbutyl)hydrazine bishydrochloride is prepared by dissolving the isolated ketazine in 30 ml of absolute ether which is deaerated with argon. This solution is added dropwise under argon to a suspension of 5.7 g (15 mmol) of lithium aluminium hydride in 150 ml of absolute ether. After refluxing for 1 hour, a dilute sodium hydroxide solution (2N) is added slowly, with cooling with ice, until no evdution of gas (H$_2$) is found anymore. After extracting the product with ether, the aqueous phase is separated and the organic phase is slowly added to 50 ml of 6N-hydrochloric acid. This hydrochloric acid solution is concentrated completely by evaporation. The white residue is recrystallised from methanol and dried in a vacuum drying oven. Yield: 2.6 g (10.6%).—M.p.: 155° C.—IR (KBr): $\nu$=3436 cm$^{-1}$ m, 3206 m [NH], 2961 s, 2934 s, 2875 s, 2036 w br., 1604 m br., 1508 m br., 1467 m br., 1384 w, 1141 w, 742 w, 578 w.

Example 10

The procedure of Example 5 is repeated using the following educts and amounts (purification and separation are carried out by column chromatography (silica gel) and using chloroform/ethanol (20:1) as eluant: 176 mg (0.450 mmol) of perylene-3,4:9,10-tetracarboxylic bisanhydride, 202 mg (0.670 mmol) of N,N'-bis(1-propylbutyl)-hydrazine bishydrochloride (from Example 9), 2.2 g of imidazole. Yield: 61 mg (23%) of N,N'-bis(1-propyl-butyl)-perylene-3,4:9,10-tetracarboxylic bis(dicarboximide).

Example 11

The procedure of Example 5 is repeated using the following educts and amounts: 910 mg (3.39 mmol) of naphthalene-1,8:4,5-tetracarboxylic bisanhydride, 273 mg (3.73 mmol) of isobutylamine, 496 mg (3.73 mmol) of N,N'-dimethylhydrazine bishydrochloride.

$1^{st}$ fraction: N,N'-dimethyl-N"-(1-methylpropyl)-naphthalene-1:4,5-tricarboxylic acid-4,5-imide-1,8-hydrazam. Yield: 0.36 g (25%), m.p.: 248° C.—$R_f$(silica gel, chloroform/ethanol 10:1)=0.19.—IR (KBr): ν=3426 cm$^{-1}$ s, 2967 w, 2935 w, 2876 w, 1684 s, 1639 s, 1589 s, 1529 s, 1499 w, 1464 w, 1398 s, 1383 s, 1346 s, 1260 m, 1224 m, 1202 w, 1106 w, 1081 w, 1038 w, 864 w, 838 w, 810 w, 754 s, 693 w, 585 w, 452 w, 422 w.—UV/vis (CHCl$_3$): $\lambda_{max}$=350.7 nm (5400), 470 (10600), 512 sh (5500).—Fluorescence (CHCl$_3$): $\lambda_{max}$=552 nm, 585, 635 sh.—Solid-state fluorescence: $\lambda_{max}$=626 nm.—Fluorescence quantum yield (CHCl$_3$): 21%, based on N,N'-(1-hexylheptyl)-perylene-3,4:9,10-bis(dicarboximide) with 100% fluorescence quantum yield.

$C_{19}H_{19}N_3O_3$ (337.4): calcd. C, 67.63; H, 5.68; N, 12.46; found C, 67.58; H, 5.41; N, 12.41.

$2^{nd}$ fraction: N,N'-dimethyl-N"-{7-(1-methylpropyl)-1,3,6,8-tetraoxo-isoquinolino[6,5,4-c,d,e]-isoquinoline-2-yl}-naphthalene-1:4,5-tricarboxylic acid-4,5-imide-1,8-hydrazam. Yield: 0.13 g (6.4%), m.p.: 253° C.—$R_f$(silica gel, chloroform/ethanol 10:1)=0.1.—IR (KBr): ν=3436 cm$^{-1}$ m, 2963 m, 2930 m, 1706 m, 1668 s, 1613 s, 1590 s, 1528 m, 1498 w, 1448 m, 1384 m, 1331 s, 1322 s, 1248 s, 1212 m, 1154 w, 1128 w, 1082 w, 1037 w, 976 w, 875 w, 828 w, 810 w, 765 m, 751 m, 692 w, 674 w, 581 w, 473 w, 406 m.—UV/vis (CHCl$_3$): $\lambda_{max}$=359.1 nm (15000), 379.5 (17000), 458.4 sh (8200), 483.7 (9000), 515.4 (5600) sh.

Example 12

The procedure of Example 5 is repeated using the following educts and amounts: 0.910 g (3.39 mmol) of naphthalene-1,8:4,5-tetracarboxylic bisanhydride, 0.742 g (3.73 mmol) of 1-hexylheptylamine, 0.496 g (3.73 mmol) of N,N'-dimethylhydrazine bishydrochloride.

$1^{st}$ fraction: N,N'-dimethyl-N"-(1-hexylheptyl)-naphthalene-1:4,5-tricarboxylic acid-4,5-imide-1,8-hydrazam. Yield: 0.32 g (20%) of a red crystal powder, m.p.: 124° C.—$R_f$(silica gel, chloroform/ethanol 10:1)=0.42.—IR (KBr): ν=3436 cm$^{-1}$ s, 2956 m, 2925 s, 285 m, 1678 s, 1637 s, 1590 s, 1527 m, 1497 w, 1464 w, 1398 m, 1381 s, 1342 m, 1261 w, 1224 w, 1108 w, 1081 w, 1037 w, 878 w, 804 w, 757 m, 693 w, 589 w, 477 w, 447 w.—UV/vis (CHCl$_3$): $\lambda_{max}$=350.6 nm (5950), 471.4 (9360), 513.4 (4650) sh.—Fluorescence (CHCl$_3$): $\lambda_{max}$=543 nm.—Fluorescence quantum yield (CHCl$_3$): 22%, based on N,N'-(1-hexylheptyl)-perylene-3,4:9,10-bis(dicarboximide) with 100% fluorescence quantum yield.

$C_{28}H_{37}N_3O_3$ (463.6): calcd. C, 72.53; H, 8.05; N, 9.07; found C, 72.49; H, 7.91; N, 8.95.

$2^{nd}$ fraction: N,N'-dimethyl-N"-{7-(1-hexylheptyl)-1,3,6,8-tetraoxo-isoquinolino[6,5,4-c,d,e]-isoquinoline-2-yl}-naphthalene-1:4, 5-tricarboxylic acid-4,5-imide-1,8-hydrazam. Yield: 0.17 g (6.7%) of a red powder, m.p.: 224° C.—$R_f$(silica gel, chloroform/ethanol 10:1)=0.16.—IR (KBr): ν=3435 cm$^{-1}$ m, 2960 m, 2927 m, 2956 m, 1707 s, 1668 s, 1615 s, 1589 s, 1528 m, 1498 w, 1450 m, 1384 m, 1331 s, 1322 s, 1248 s, 1213 m, 1194 w, 1153 w, 1128 w, 1104 w, 1037 w, 977 w, 876 w, 828 w, 813 w, 766 m, 751 m, 692 w, 674 w, 473 w, 407 m.—UV/vis (CHCl$_3$): $\lambda_{max}$=359.5 nm (19000), 379.8 (22000), 459.1 sh (7500), 483.8 (9000), 516.8 (5400) sh.

$C_{42}H_{41}N_5O_7$ (727.8): calcd. C, 69.29; H, 5.68; N, 9.62.—found C, 68.94; H, 5.88; N, 9.09.

Example 13

The procedure of Example 5 is repeated using the following educts and amounts: 0.126 g (0.218 mmol) of N-(1-hexylheptyl)-perylene-3,4:9,10-tetracarboxylic-3,4-anhydride-9,10-imide, 0.115 g (0.870 mmol) of dimethylhydrazine bishydrochloride in 1 g of imidazole at 135–150° C. under argon. The product is first prepurified by column chromatography with silica gel and chloroform/acetone (20:1) and the pure fractions are then enriched by being subjected four times to chromatography via MPLC (36 bar, using CHCl$_3$ as eluant).

$1^{st}$ fraction: N-(1-hexylheptyl)-N'-methylperylene-3,4:9,10-bis(dicarboximide); yield: 7 mg (5%) of a red powder, m.p. >320° C.—$R_f$(silica gel, chloroform)=0.43.—IR (KBr): ν=3441 cm$^{-1}$ w, 2958 s, 2927 s, 2858 m, 1700 s, 1661 s, 1597 s, 1571 s, 1506 w, 1466 m, 1447 m, 1405 s, 1339 s, 1254 m, 1175 m, 1131 w, 1114 w, 1019 w, 853 m, 810 s, 799 w, 747 m.—UV/vis (CHCl$_3$): $\lambda_{max}$=432 nm (6300), 457 (19800), 488 (52300), 525 (85900).—Fluorescence (CHCl$_3$): $\lambda_{max}$=536 nm, 573, 621.—Fluorescence quantum yield (CHCl$_3$): 98%, based on N,N'-(1-hexylheptyl)-perylene-3,4:9,10-bis(dicarboximide) with 100% fluorescence quantum yield.

$2^{nd}$ fraction: 9-(1-hexylheptyl)-1,2-dihydro-1,2-dimethylanthraceno[3,4,5-c,d,e]isoquinolino-[7,6,5-d,e,f]cinnoline-3,8,9-trione or N"-(1-hexylheptyl)-N,N'-dimethylperylene-3:9,10-tricarboxylic acid-9,10-imide-3,4-hydrazam; yield: 46 mg of a blue solid (36%), m.p. 301° C.—$R_f$(silica gel, chloroform)=0.16.—IR (KBr): ν=3444 cm$^{-1}$ m, 2956 m, 2926 s, 2856 m, 1688 m, 1649 s, 1610 w, 1570 s, 1505 m, 1461 w, 1398 w, 1391 w, 1350 s, 1288 s, 1258 w, 1220 w, 802 m, 751 w, 731 w.—UV/vis (CHCl$_3$): $\lambda_{max}(\epsilon)$=397.3 nm (5160), 572.5 (26800)—Fluorescence (CHCl$_3$): $\lambda_{max}$=725.1 nm, 804.8.—Fluorescence quantum yield (CHCl$_3$): 6%, based on N,N'-(1-hexylheptyl)-perylene-3,4:9,10-bis(dicarboximide) with 100% fluorescence quantum yield.

$C_{38}H_{41}N_3O_3$ (587.8): calcd. C, 77.64; H, 7.04; N, 7.15; found C, 77.06; H, 7.07; N, 7.20.

$3^{rd}$ fraction: N-(1-hexylheptyl)-N'-methylaminoperylene-3,4:9,10-bis(dicarboximide); chromatography: The product is first prepurified by column chromatography with silica gel and chloroform/acetone (20:1) and the pure fractions are then enriched by being purified four times via MPLC (36 bar, using CHCl$_3$ as eluant): yield: 37 g (28%) of a red powder, m.p. >320° C.—$R_f$(silica gel, chloroform)=0.17.—IR (KBr): ν=3430 cm$^{-1}$ w, 2952 w, 2926 w, 2851 w, 1700 s, 1685 m, 1653 s, 1636 m, 1594 s, 1577 m, 1506 m, 1506 w, 1457 w, 1437 w, 1404 m, 1342 s, 1257 m, 1166 m, 809 s, 742 m, 668 m.—UV/vis (CHCl$_3$): $\lambda_{max}\epsilon$=459 (18000), 490 (51000), 527 nm (81200).—Fluorescence (CHCl$_3$): $\lambda_{max}$=537nm, 573, 621 sh.

$C_{38}H_{38}N_2O_4$ (601.3): calcd. C, 75.84; H, 6.54; N, 6.99; found C, 75.16; H, 6.64; N, 6.66.

Example 14

The procedure of Example 5 is repeated using the following educts and amounts: 0.116 g (0.201 mmol) of N-(1-hexylheptyl)-perylene-3,4:9,10-tetracarboxylic-3,4-anhydride-9,10-imide, 0.121 g (0.402 mmol) of diheptylhydrazine in 1 g of imidazole at 135–150° C. under argon. Chromatography: The product is first prepurified by column chromatography with silica gel and chloroform/acetone (20/1). The monoimide and the bisimide are again subjected to chromatography using $CHCl_3$ as eluant. The blue hydrazamimide is chromatographed with $CH_2Cl_2$/acetone (40/1) and the ice-blue hydrazamaminoimide is chromatographed with $CH_2Cl_2$/acetone (20/1). The aminoimide imide is chromatographed with chloroform/acetone (15/1) and the bis(aminoimide) is chromatographed with chloroform/ethanol (10/1).

$1^{st}$ fraction: N-(1-hexylheptyl)-perylene-3,4-dicarboximide: yield: 1 mg (1%).

$2^{nd}$ fraction: N-heptyl-N'-(1-hexylheptyl)-perylene-3,4:9,10-bis(dicarboximide): yield: 8 mg (6%) of a red powder, m.p.: 198° C.—$R_f$(silica gel, chloroform)=0.74.—IR (KBr): $\nu$=2955 $cm^{-1}$ m, 2926 s, 2856 m, 1698 s, 1658 s, 1594 s, 1579 m, 1507 w, 1465 w, 1457 w, 1406 m, 1378 w, 1339 s, 1253 m, 1210 w, 1174 m, 1124 w, 1108 w, 960 w, 850 w, 810 m, 795 w, 747 m, 725 w.—UV/vis ($CHCl_3$): $\lambda_{max}\epsilon$=458.1 (18300), 488.9 (50300), 525.5 nm (84300).—Fluorescence ($CHCl_3$): $\lambda_{max}$=537 nm, 575, 621.—Fluorescence quantum yield ($CHCl_3$): 99%, based on N,N'-(1-hexylheptyl)-perylene-3,4:9,10-bis(dicarboximide) with 100% fluorescence quantum yield.

$C_{44}H_{50}N_2O_4$ (670.4): calcd. C, 78.67; H, 7.52; N, 4.18; found C, 77.99; H, 7.81; N, 3.99.

$3^{rd}$ fraction: N-heptyl-N'-(1-hexylheptyl)-3-aminoperytene-4:9,10-tricarboxylic acid-3,4-lactam-9,10-imide: yield: 5 mg (4%) of a violet solid, m.p. 243° C.—$R_f$(silica gel, chloroform/acetone (10:1))=0.47.—IR (KBr): $\nu$=3436 $cm^{-1}$ m, 2956 m, 2928 m, 2856 m, 1696 s, 1659 s, 1595 s, 1579 w, 1508 w, 1440 w, 1404 m, 1381 w, 1345 s, 1250 w, 1092 w, 854 w, 810 m, 746 m.—UV/vis ($CHCl_3$): $\lambda_{max}$(E)=362.8 nm (4900), 391.4 (7300) sh, 410.6 (8500), 444.8(5900) sh, 493.3 (14500) sh, 529.2 (24000), 578.9 (16100) sh.—Fluorescence ($CHCl_3$): $\lambda_{max}$=610 nm.— $C_{43}H_{50}N_2O_3$: calcd. 642.3821; found 642.3809 (MS).

$4^{th}$ fraction: 1,2-diheptyl-9-(1-hexylheptyl)-1,2-dihydro-anthraceno[3,4,5-c,d,e]isoquinolino-[7,6,5-d,e,f]cinnoline-3,8,9-trione or N,N'-diheptyl-N''-(1-hexylheptyl)-perylene-3:9,10-tricarboxylic acid-9,10-imide-3,4-hydrazam: yield: 41 mg (27%) of a blue solid, m.p.: 154° C.—$R_f$(silica gel, chloroform/acetone 10:1)=0.39.—IR (KBr): $\nu$=3444 $cm^{-1}$ m, 2955 s, 2929 s, 2857 s, 1686 s, 1650 s, 1609 w, 1570 s, 1505 m, 1460 w, 1396 w, 1391 w, 1348 s, 1287 s, 1256 w, 1219 w, 802 m, 752 w, 731 w.—UV/vis ($CHCl_3$): $\lambda_{max}\epsilon$= 403.0 nm (3870), 587.6 (22000).—Fluorescence ($CHCl_3$): $\lambda_{max}$=726.4 nm, 805.0 sh.—Fluorescence quantum yield ($CHCl_3$): 7%, based on N,N'-(1-hexylheptyl)-perylene-3,4:9,10-bis(dicarboximide) with 100% fluorescence quantum yield. $C_{50}H_{65}N_3O_3$: calcd. 755.5026; found 755.5051 (MS).

$5^{th}$ fraction: N-heptylamino-N'-(1-hexylheptyl)-perylene-3,4:9,10-bis(dicarboximide): yield: 44 mg (32%) of a reddish black solid—m.p.: 191° C.—$R_f$(silica gel, chloroform/ethanol 10:1)=0.41.—IR (KBr): $\nu$=3436 $cm^{-1}$ s, 2956 s, 2926 s, 2856 s, 1698 s, 1657 s, 1594 s, 1578 m, 1507 w, 1458 w, 1404 s, 1343 s, 1254 m, 1176 m, 1127 w, 852 m, 810 m, 742 m.—UV/vis ($CHCl_3$): $\lambda_{max}(\epsilon)$=431.3 nm (5800), 459.6 (15700), 490.5 (39200), 527.2 (63700)—fluorescence ($CHCl_3$): $\lambda_{max}$=541 nm, 576.

$C_{44}H_{51}N_3O_4$ (685.9): calcd. C, 77.04; H, 7.50; N, 6.13; found C, 76.82; H, 7.54; N, 5.98.

Example 15:

500 mg (1.97 mmol) of naphthalene-1,4:5,8-tetracarboxylic bisanhydride, 0.99 g (7.5 mmol) of N,N'-dimethylhydrazine bishydrochloride, 10 ml of DMF. This reaction mixture is heated under argon for 2 h in 10 ml of DMF to 145° C. The major part of the solvent is then stripped off under vacuum (remainder about 1 ml). The batch is then boiled in 100 ml of 2N-HCl and after filtration the residue is dried at 120° C. overnight in a drying oven. The pale brown product obtained is made into a slurry in 200 ml of $CHCl_3$ and is then dissolved by heating and purified by chromatography.

$1^{st}$ fraction: N-methyl-N'-(dimethylamino)-naphthalene-1,4:5,8-bis(dicarboximide): yield: 82.7 mg (13%).—IR (KBr): $\nu$=3436 $cm^{-1}$ m, 2917 w, 2860 w, 1702 m (C=O), 1661 s (C=O), 1580 w, 1453 w, 1372 w, 1245 m, 1182 w, 1091 w, 769 m.—UV/vis ($CHCl_3$): $\lambda_{max}(\epsilon)$=359.6 nm (19100), 380.3 (19400).

$C_{17}H_{13}N_3O_4$ (323.3): calcd. C, 63.13; H, 4.05; N, 13.00; found C, 62.78; H, 4.18; N, 12.96.

$2^{nd}$ fraction: N-methyl-N'-(methylamino)-naphthalene-1,4:5,8-bis(dicarboximide): yield: 194.8 mg (32%).—IR (KBr): $\nu$=3436 $cm^{-1}$ m, 2919 w, 2856 w, 1702 m (C=O), 1660 s (C=O), 1582 w, 1453 w, 1374 w, 1344 m, 1246 m, 1183 w, 1093 w, 768 m, 570 w.—UV/vis ($CHCl_3$): $\lambda_{max}(\epsilon)$= 359.4 nm (19000), 380.1 (20000).

$C_{16}H_{11}N_3O_4$ (309.3): calcd. C, 62.12; H, 3.89; N, 13.59; found C, 61.94; H, 3.64; N, 13.53.

Example 16

0.86 g (6.5 mmol) of dimethylhydrazine bishydrochloride and 0.59 g (2.2 mmol) of naphthalene-1,8:4,5-tetracarboxylic bisanhydride are dissolved in 4 g of melted imidazole and heated for 2 hours at 130° C. After cooling, about 40 ml of ethanol are added and hydrolysis is carried out using a mixture of 100 ml of dilute hydrochloric acid and 200 ml of water. An orange red precipitate forms which is briefly boiled in the aqueous solution, the residue then being left standing for 5 hours. The crude product is then collected by filtration. The dye is taken up in 500 ml of chloroform and boiled. This solution is subjected to hot filtration and is then concentrated by evaporation to 200 ml. After column chromatography, the yields are extrapolated to the entire product. The compounds are sparingly soluble. The eluant used is chloroform/acetone (15/1). The first and second fraction are eluted first, after which the eluant (chloroform/ethanol (10/1)) is changed and a third and fourth fraction are eluted. A fifth and sixth fraction are first eluted using chloroform/ethanol (3/1). Even when using pure ethanol as eluant, part of the dye mixture remains firmly adsorbed to the silica gel. The first fraction is not worked up any further as it only has the bisimide bands in the UV/vis spectrum and in the mass spectrum has the mass of N,N'-dimethylnaphthalene-1,8:4,5-bis(dicarboximide) which is known from the literature. The compound yield is 6.0 mg (0.93%). The second fraction is purified twice by column chromatography with $CH_2Cl_2$/acetone (20/1) as eluant. The orange fluorescent compound is identified as N,N',N''-trimethylnaphthalene-1:4,5-tricarboxylic acid-4,5-imide-1,8-hydrazam. From the third fraction the compound N-methyl-N'-methylaminonaphthalene-1,8:4,5-bis (dicarboximide), discussed in the above example 15, is isolated in a yield of 20 mg (3%). The fourth fraction is chromatographed using CHCl$_3$ethanol (10/1) and is separated into two fractions which are further purified using the same eluant. This compound is the non-fluorescent bichromophoric compound N,N'-dimethyl-N"-{7-methylamino-1,3,6,8-tetraoxo-isoquinolino[6,5,4-c,d,e]isoquinoline-2-yl}-naphthalene-1:4,5-tricarboxylic acid-4,5-imide-1,8-hydrazam and the highly fluorescent bichromophoric compound N,N'-dimethyl-N"-{1,2-dihydro-1,2-dimethyl-3,6,8-trioxo-isoquinolino[6,5,4-d,e,f]cinnoline-7-yl}-naphthalene-1:4,5-tricarboxylic acid-4,5-imide-1,8-hydrazam. No products can be identified from the last two fractions.

1$^{st}$ fraction: N,N',N"-trimethyinaphthalene-1:4,5-tricarboxylic acid-4,5-imide-1,8-hydrazam; yield: 36 mg (5.6%) of a red pigment, m.p.: >320° C.—R$_f$(silica gel/chloroform/ethanol (5/2))=0.63.—IR (KBr): ν=3435cm$^{-1}$ s, 2922 w, 2852 w, 1679 m, 1638 s, 1590 s, 1528 w, 1499 w, 1465 w, 1404 w, 1384 m, 1354 w, 1280 w, 1260 w, 1232 w, 1165 w, 1108 w, 1048 w, 814 w, 750 m.—UV/vis (CHCl$_3$): λ$_{max}$(ε)=352.1 (5880) nm, 374.6 sh (3800), 453.5 sh (8500), 474.5 (9100), 514.8 sh (5100).—Fluorescence (CHCl$_3$): λ$_{max}$=543 nm, 567 sh.—Fluorescence quantum yield (CHCl$_3$): 19%, based on N,N'-(1-hexylheptyl)-perylene-3,4:9,10-bis(dicarboximide) with 100% fluorescence quantum yield.

C$_{16}$H$_{13}$N$_3$O$_3$ (295.3): calcd. C, 65.06; H, 4.44; N, 14.24; found C, 63.62; H, 4.38; N, 13.72.

2$^{nd}$ fraction: N,N'-dimethyl-N"-{7-methylamino-1,3,6,8-tetraoxo-isoquinolino[6,5,4-c,d,e]-isoquinoline-2-yl}-naphthalene-1:4,5-tricarboxylic acid-4,5-imide-1,8-hydrazam; yield: 43 mg (3.4%) of a red pigment, m.p.: >320° C.—R$_f$(silica gel/chloroform/ethanol (5/2))=0.6.—IR (KBr): ν=3435 cm$^{-1}$ m, 3081 w, 2927 w, 1707 s, 16667 s, 1615 m, 1586 s, 1528 m, 1498 m, 1452 m, 1393 m, 1341 s, 1321 s, 1289 m, 1243 s, 1218 m, 1196 w, 1154 m, 1129 w, 1107 w, 1045 w, 988 w, 966 w, 879 w, 860 w, 828 w, 810 w, 764 m, 751 m, 692 w 564 w, 473 w, 418 w.—UV/vis (CHCl$_3$): λ$_{max}$(ε)=358.4 nm (26800), 378.6 (30400), 457.7 sh (11500), 483.6 (13200), 516.9 sh (8500).

C$_{30}$H$_{18}$N$_6$O$_7$ (574.5): calcd. C, 62.70; H, 3.16; N, 14.63; found C, 63.24; H, 3.00; N, 12.11.

3$^{rd}$ fraction: N,N'-dimethyl-N"-{1,2-dihydro-1,2-dimethyl-3,6,8-trioxo-isoquinolino[6,5,4-d,e,f]cinnolin-7-yl}-naphthalene-1:4,5-tricarboxylic acid-4,5-imide-1,8-hydrazam; yield: 58 mg (4.7%) of an intensely red pigment, m.p.: >320° C.—R$_f$(silica gel, chloroform/ethanol (5/2))=0.34.—IR (KBr): ν=3435 cm$^{-1}$ m, 2925 w, 1694 s, 1663 s, 1614 s, 1586 s, 1528 m, 1497 m, 1464 w, 1379 s, 1340 m, 1323 s, 1218 m, 1105 w, 1034 w, 952 w, 866 w, 830 w, 807 w, 748 m, 692 w, 671 w, 564 w, 474 w, 416 w.—UV/vis (CHCl$_3$): λ$_{max}$(ε)=355.4 nm (7850), 378.2 sh (5540), 459.2 sh (9260), 484.2 (10900), 516.9 sh (7430).—Fluorescence (CHCl$_3$) λ$_{max}$=545 nm, 585 sh.

C$_{30}$H$_{20}$N$_6$O$_6$: calcd. 560.1444; found 560.1480 (MS).

Example 17

0.22 g (0.57 mmol) of perylene-3,4:9,10-tetracarboxylic bisanhydride, 0.337 g (2.51 mmol) of N,N'-dimethylhydrazine bishydrochloride and 2 g of imidazole are reacted at 135–150° C. under argon. The customary working up yields a violet black pigment mixture. The products are completely insoluble in the majority of the solvents. When being boiled in DMSO, the perylenebisimide dissolves better than the perylene-imide-hydrazam as the corresponding UV/vis spectra show. Yield: 0.25 g of a violet black pigment mixture, m.p: >320° C.—IR (KBr): ν=3439 cm$^{-1}$ m, 2980 w br., 1766 w, 1695 s, 1658 s, 1616 w, 1594 s, 1579 s, 1507 w, 1457 m, 1400 s, 1358 s, 1324 w, 1285 m, 1238 w, 1165 w, 1054 w, 871 w br., 810 s, 744 m, 605 w, 435 s, 409 w.—UV/vis (glacial acetic acid): λ$_{max}$(rel. I)=351.4 nm (0.94), 457.1 (0.93), 487.0 (0.95), 522.5 (1.00), 587.9 (0.95).

Example 18

0.500 g (1.28 mmol) of perylene-3,4:9,10-tetracarboxylic acid-9,10-imide-3,4-anhydride, 0.51 g (3.8 mmol) of N,N'-dimetylhydrazine bishydrochloride and 3 g of imidazole are reacted at 135–150° C. under argon. Customary working up yields a violet black pigment mixture. Yield: 0.52 g, m.p.: >320° C.—IR (KBr): ν=3443 cm$^{-1}$ m, 2987 w br., 1692 s, 1656 s, 1614 w, 1593 s, 1578 s, 1507 w, 1458 m, 1401 s, 1359 s, 1347 m, 1324 w, 1273 m, 1162 w, 1058 w, 871 w br., 810 s, 794 m, 744 w, 656 m, 435 s, 409 w.—UV/vis (glacial acetic acid): λ$_{max}$(rel. I)=350.9 nm (0.95), 457.3 (0.89), 487.2 (0.90), 522.5 (1.00), 587.9 (0.97).

Example 19

The procedure of Example 5 is repeated using the following educts and amounts: 1.0 g (4.12 mmol) of 4-nitronaphthalene-1,8-dicarboxylic anhydride, 1.00 g (7.52 mmol) of N,N'-dimethylhydrazine bishydrochloride. Yield: 0.4 g (38%) of a yellow powder consisting of 1,2-dihydro-1,2-dimethyl-6-nitrobenzo,[2,3-d,e]cinnolin-3-one and 1,2-dihydro-1,2-dimethyl-7-nitrobenzo[1,2,3-d,e]cinnolin-3-one.—R$_f$(silica gel, chloroform/ethanol (10:1))=0.3.—UV/vis (CHCl$_3$): λ$_{max}$(ε)=442.9 nm (644).—Fluorescence (CHCl$_3$): none.

C$_{113}$H$_{11}$N$_3$O$_3$: calcd. 257.0800; found 257.0802 (MS).

Example 20

0.500 g (1.87 mmol) of naphthalene-1,8:4,5-tetracarboxylic bisanhydrde , 0.221 g (2.05 mmol) of o-phenylenediamine, 0.582 g (2.05 mmol) of N,N'-dinonylhydrazine and 3 g of imidazole are first refluxed for 1½ h under argon at 140° C. The temperature is then increased for 2 h to 170° C. After cooling to about 100° C., the batch is poured in 100 ml of 2N-HCl and boiled for 30 min. The reaction mixture is then left standing for 6 h to cool and age. After filtration (over a D4 frit), the intensely red crude product is dried overnight in a drying oven at 120° C. The dye mixture is chromatographed using CHCl$_3$ acetone (15/1) and separated into five fractions.

1$^{st}$ fraction: 1,2-dihydro-1,2-dinonylbenzimidazolo[2,1-j]isoquinolino[6,5,4-d,e,f]cinnoline-3,11-dione; yield: 117 mg (11%), m.p. 82° C.—R$_f$(silica gel, toluene/chloroform/ethanol (12/8/1))=0.28.—IR (KBr): ν=3435 cm$^{-1}$ m, 3056 w, 2957 m, 2924 s, 2854 s, 1686 s, 1644 s, 1613 w, 1596 s, 1551 s, 1522 m, 1467 s, 1451 s, 1428 w, 1409 w, 1398 w, 1376 m, 1347 m, 1310 m, 1286 w, 1254 w, 1237 w, 1202 w, 1179 w, 1145 w, 1110 w, 1099 w, 1085 w, 1026 w, 1010 w, 969 w, 939 w, 877 w, 828 w, 816 w, 757 s, 722 w, 714 w, 642 w, 598 w, 501 w, 470 w.—UV/vis (CHCl$_3$): λ$_{max}$(ε)=348.1 nm (15100), 519.6 (11400).

C$_{37}$H$_{46}$N$_4$O$_2$ (578.8): calcd. C, 76.77; H, 8.02; N, 9.68; found C, 76.69; H, 8.43; N, 9.57.

The second fraction is chromatographed with tolouene/CHCl$_3$/EtOH (12:8:1). The main product obtained from this fraction is the violet 1,2-dihydro-1,2-dinonylbenzimidazolo[2,1-j]isoquinolino[6,5,4-d,e,f]cinnoline-3,11-dione. Yield: 0.112 g (11%), m.p. 86° C.—R$_f$(silica gel, chloroform/ethanol (10:1))=0.40.—IR (KBr): ν=3436 cm$^{-1}$ m, 3056 w, 2957 s, 2925 s, 2854 s, 1678 s, 1654 s, 1613 s, 1582 s, 1556 m, 1518 s, 1467 m, 1451 w, 1428 w, 1416 m, 1397 m, 1374 m, 1350 s, 1314 w, 1287 w, 1265 w, 1242 m, 1214 w, 1179 m, 1153 m, 1116 m, 1099 w, 1085 w, 1026 w, 848 w, 801 w, 752 s, 723 w, 685 w, 619 w, 468 w, 439 w.—UV/vis (CHCl$_3$): $\lambda_{max}(\epsilon)$=356.2 nm (9300), 377.5 (7800), 460.5 sh (1 5900), 485.3 (20300), 511.1 sh (16000).—Fluorescence (CHCl$_3$, corrected): $\lambda_{max}$=544 nm, 579, 636 sh.—Fluorescence quantum yield (CHCl$_3$): 77%, based on N,N'-(1-hexylheptyl)-perylene-3,4:9,10-bis(dicarboximide) with 100% fluorescence quantum yield.

C$_{37}$H$_{46}$N$_4$O$_2$ (578.8): calcd. C, 76.77; H, 8.02; N, 9.68; found C, 76.32; H, 7.77; N, 9.50.

The third fraction is chromatographed with CHCl$_3$/EtOH (10:1). The main product obtained from this fraction is the intensely red 1,2-dihydro-1,2-dinonylbenzimidazolo[1,2-a]isoquinolino[6,5,4-d,e,f]cinnoline-3,6-dione. Yield: 0.083 2(9%), m.p.: 233° C.—R$_f$(silica gel, chloroform/ethanol (10:1))=0.31.—IR (KBr): $\nu$=3431 cm$^{-1}$ m, 3078 w, 2955 m, 2925 s, 2855 s, 17160 s, 1670 s, 1614 w, 1582 m, 1551 w, 1509 w, 1466 w, 1447 m, 1404 w, 1377 s, 1350 s, 1313 m, 1244 s, 1180 w, 1121 w, 1068 w, 1010 w, 989 w, 877 w, 826 w, 800 w, 761 s 734 w, 707 w, 589 w, 468 w, 435 w, 418 w.—UV/vis (CHCl$_3$): $\lambda_{max}(\epsilon)$=356.8 nm (10600), 442.0 (13700).—Fluorescence (CHCl$_3$): $\lambda_{max}$=532.5 nm.—Fluorescence quantum yield (CHCl$_3$): 14%, based on N,N'-(1-hexylheptyl)-perylene-3,4:9,10-bis(dicarboximide) with 100% fluorescence quantum yield.—Solid-state fluorescence: $\lambda_{max}$=563 nm.

C$_{29}$H$_{28}$N$_4$O$_3$ (480.6): calcd. C, 72.47; H, 5.88; N, 11.66; found C, 72.22; H, 5.70; N, 11.53.

The fourth fraction is chromatographed with CHCl$_3$/glacial acetic acid (10/1). The main product obtained from this fraction is the orange 2-nonylaminobenzimidazolo[2,1-j]isoquinolino-[6,5,4-c,d,e]isoquinoline-1,3,11-trione.

Example 21

500 mg (1.87 mmol) of naphthalene-1,8:4,5-tetracarboxylic bisanhydride, 0.325 g (2.06 mmol) of naphthalene-1,8-diamine, 0.582 g (2.05 mmol) of N,N'-dinonylhydrazine and 3 g of imidazole are reacted. Working up is carried out as above. After drying at elevated temperature, 0.85 g of a blue pigment mixture is obtained. This mixture is extracted for three hours with hot chloroform. The blue pigment mixture remains in the extraction thimble. The thimble with the pigment mixture is dried in a drying oven at 70° C. 0.25 g of pigment mixture (26%) is thus obtained. The CHCl$_3$ solution obtained through the extraction of the crude product is purified by column chromatography after cooling. For rough separation and prepurification the product is chromatographed with CHCl$_3$/acetone (15:1) over silica gel.

Four main fractions are obtained:

The first fraction is chromatographed first with CHCl$_3$/acetone (15:1) and then with CHCl$_3$/toluene/ethanol (16:12:1). Yield: 0.25 g (26%), m.p.: >320° C.—IR (KBr): $\nu$=3435 cm$^{-1}$ m, 3055 w, 2923 w, 2852 w, 1779 s, 1742 m, 1681 s, 1624 m, 1599 s, 1522 w, 1500 w, 1456 w, 1396 m, 1369 w, 1344 w, 1318 w, 1287 m, 1258 s, 129 m, 1172 m, 1109 m, 1074 w, 1018 w, 867 w, 847 w, 826 s, 766 s, 750 s, 727 w, 724 w.—UV/vis (glacial acetic acid): $\lambda_{max}$(rel. I)=352.1 nm (1.0), 370.9 (0.9), 395.9 (0.5) sh, 494.0 (0.3) sh, 550.4 (0.4), 598.3(0.3 )sh, 658.9 (0.2) sh. C$_{34}$H$_{16}$N$_4$O$_2$ calcd. 512.1273, found 512.1270 (MS).

The second fraction is chromatographed with CH$_2$Cl$_2$/acetone (20:1). The violet 1,2-dihydro-1,2-dinonylcinnolino[6,7,8-c,d,e]isoquinolino[2,3-b]perimidine-3,13-dione is isolated from this fraction. Yield: 0.25 g (21%), m.p.: 147° C.—R$_f$(silica gel, chloroform/toluene/ethanol (8/12/1))= 0.53.—R$_f$(silica gel, methylene chloride/acetone (20/1))= 0.69.—IR (KBr): $\nu$=3436 cm$^{-1}$ s, 2952 m, 2923 s, 2853 s, 1673 s, 1652 s, 1618 s, 1594 m, 1572 m, 1552 m, 1528 m, 1500 w, 1467 m, 1414 w, 1399 m, 1370 w, 1349 m, 1321 m, 1285 w, 1245 w, 1226 w, 1171 w, 1140 w, 1113 m, 1071 w, 859 w, 826 m, 768 m, 748 m, 722 w.—UV/vis (CHCl$_3$): $\lambda_{max}(\epsilon)$=354.2 nm (7030), 425.7 (5350), 530.7 (11700), 552.5 (11300) sh.—Fluorescence (CHCl$_3$): $\lambda_{max}$=585.4 nm, 650.8 sh. C$_{41}$H$_{48}$N$_4$O$_2$: calcd. 628.3777; found 628.3788 (MS).

The third fraction is purified in a Chromatotron model 7924T (of Harrison Research, 840 Moana Court, Palo Alto, Calif., USA) using CH$_2$Cl$_2$/acetone as eluant. The blue 12-nonylamino-isoquinolino[6,5,4-c,d,e]isoquinolino[2,3-b]perimidine-8,11,13-trione may be isolated from this fraction. Yield: 0.31 g (31%), m.p.: 248° C.—R$_f$(silica gel, chloroform/toluene/ethanol (8/12/1))=0.27. IR (KBr): $\nu$=3436 cm$^{-1}$ m, 3049 w, 2923 m, 2852 m, 1709 m, 1667 s, 1626 m, 1597 m, 1555 w, 1500 w, 1456 w, 1395 w, 1337 m, 1318 m, 1256 s, 1231 m, 1182 w, 1119 w, 1110 m, 1080 w, 1069 w, 1006 w, 989 w, 868 w, 846 w, 824 m, 758 m, 748 m, 727 w, 702 w.—UV/vis (CHCl$_3$): $\lambda_{max}(\epsilon)$=376.1 nm (16600), 559.6 (10190), 595.4 (11100), 666.6 (6100) sh.—Fluorescence (CHCl$_3$): $\lambda_{max}$=555 nm, 602 sh, 722.

C$_{33}$H$_{30}$N$_4$O$_3$ (530.6): calcd. C, 74.68; H, 5.70; N, 10.56; found C, 74.20; H, 5.24; N, 10.46.

Example 22

1.00 g (3.73 mmol) of naphthalene-1,8:4,5-tetracarboxylic bisanhydride, 648 mg (4.11 mmol) of naphthalene-1,8-diamine, 511 mg (4.11 mmol) of tert-butylhydrazine hydrochloride and 3 g imidazole are reacted. The synthesis and working up are carried out in analogy to Example 5. The reaction mixture is chromatographed in CHCl$_3$/EtOH (20/1) over silica gel. Yield: 0.562 g (0.33%) of 12-tert-butylamino-isiquinolino-[6,5,4-c,d,e]isoquinolino-[2,3-b]-perimidine-8,11,13-trione, m.p.: >320° C.—R$_f$(silica gel, chloroform/ethanol (20: 1))=0.57.—IR (KBr): $\nu$=3437 cm$^{-1}$ s, 3109 w, 2967 m, 2927 w, 2873 w, 1715 s, 1674 s, 1627 m, 1601 m, 1558 m, 1521 w, 1501 w, 1458 m, 1368 w, 1325 s, 1256 s, 1235 m, 1207 w, 1184 m, 1143 w, 1111 w, 1079 w, 1044 w, 1008 m, 988 w, 872 w, 848 w, 826 m, 764 m,—UV/vis (CHCl$_3$): $\lambda_{max}(\epsilon)$=373.8 nm (16000), 556.1 (10000) sh, 591.1 (11000), 661.6 (6000) sh.—Fluorescence (CHCl$_3$): $\lambda_{max}$=535 nm, 576, 634, 753.

C$_{28}$H$_{20}$N$_4$O$_3$(460.5): calcd. C, 73.02; H, 4.38; N, 12.17; found C, 73.16; H, 4.3.9; N, 11.98.

Example 23

1.00 g (3.73 mmol) of naphthalene-1,8:4,5-tetracarboxylic bisanhydride, 0.403 g (3.73 mmol) of o-phenylenediamine, 0.224 g (3.73 mmol) of N,N'-dimethylhydrazine and 3 g of imidazole are reacted in analogy to Example 5. The resulting reaction mixture is chromatographed in CHCl$_3$/EtOH (10/1) over silica gel. The eluant (CHCl$_3$/EtOH (5/2) is then changed. Four fractions are obtained: the first fraction is chromatographed with CHCl$_3$/acetone (15/1). The yellow pigment 2-methylbenzo[lmn]benzimidazolo[1,2j][3,8]-phenanthroline-1,3,6-trione is obtained from this fraction; yield: 98 mg (7%), m.p. >320° C.—R$_f$(silica gel, chloroform/ethanol (10:1))=0.23. —IR (KBr): $\nu$=3433 cm$^{-1}$ (m), 3079 (w), 2926 (w), 1706 (s), 1666 (s), 1616 (w), 1583 (w), 1550 (w), 1508 (w), 1448 (m), 1420(w), 1377 (m), 1350 (s), 1313 (m), 1288 (m), 1239 (m), 1173 (w), 1152 (w), 1047 (m), 1009 (w), 974 (w), 953 (w), 863 (w), 765 (s), 732 (w), 588 (w), 579 (w).—UV/vis (CHCl$_3$): $\lambda_{max}(\epsilon)$=370.1 nm (9277), 440.8 (13576).—Fluorescence (CHCl$_3$): $\lambda_{max}$=540 nm.—Fluorescence quantum yield (CHCl$_3$): 15%, based on N,N'-(1-hexylheptyl)-perylene-3,4:9,10-bis(dicarboximide) with 100% fluorescence quantum yield.—Solid-state fluorescence: $\lambda_{max}$=596 nm.

$C_{21}H_{11}N_3O_3$ (353.3): calcd. C, 71.36; H, 3.14, N, 11.90; found C, 71.00; H, 3.29; N, 11.72.

The second fraction is chromatographed with CHCl$_3$/EtOH (10:1). The red pigment 1,2-dihydro-1,2-dimethylbenzimidazolo[2,1j]isoquinolino[6,5,4-d,e,f]cinnoline-3,11-dione is isolated. Yield: 0.21 (16%)—m.p.: >320° C.—R$_f$(silica gel, chloroform/ethanol (5:2))=0.52.—IR (KBr): $\nu$=3436 cm$^{-1}$ s, 2924 m, 2853 w, 1670 s, 1613 s, 1584 s, 1545 m, 1519 s, 1449 w, 1384 s, 1350 s, 1318 m, 1289 m, 1265 m, 1244 m, 1215 w, 1148 w, 1106 w, 1037 w, 894 w, 798 w, 756 s, 694 w, 575 w, 472 w.—UV/vis (CHCl$_3$): $\lambda_{max}(\epsilon)$=356.5 (7200), 376.6 (200), 453.5 (10400) sh, 480.5 (13200), 508.3 (10200).—Fluorescence (CHCl$_3$, corrected): $\lambda_{max}$=544 nm, 579, 636 sh. $C_{21}H_{14}N_4O_2$: calcd. 354.1117, found 354.1145 (MS).

The third and fourth fractions are chromatographed with CHCl$_3$/EtOH (5:2). A mauve pigment mixture is isolated from these fractions: 1,2-dihydro-1,2-dimethylbenzimidazolo[2,1-j]-isoquinolino[6,5,4-d,e,f]cinnoline-3,11-dione and 1,2-dihydro-1,2-dimethylbenzimidazolo[1,2-a]isoquinolino-[6,5,4-d,e,f]cinnoline-3,6-dione (the integrals in the $^1$H-spectrum show that a mixture ratio of about 1/1 is obtained): yield: 0.45 g (34%), m.p.: >320° C.—R$_f$(silica gel, chloroform/ethanol (5:2))=0.52.—IR (KBr): $\nu$=3426 cm$^{-1}$ s, 2926 w, 2832 w, 1680 s, 1651 s, 1614 s, 1586 s, 1547 m, 1520 m, 1449 m, 1387 s, 1370 m, 1351 m, 1316 m, 1287 m, 1254 m, 1215 w, 1176 w, 1158 w, 1107 w, 1037 w, 1008 w, 965 w, 895 w, 833 w, 797 w, 756 s, 694 w, 575 w, 499 w, 474 w, 444 w.—UV/vis (CHCl$_3$): $\lambda_{max}(\epsilon)$=351.2 nm (12272), 454.1 (10250), 485.0 (15026), 509.0 (14299), 585.3 (3253) sh.

$C_{21}H_{14}N_4O_2$ (354.4): calcd. C, 71.16; H, 3.98; N, 15.82; found C, 69.86; H, 4.17; N, 15.53.

Example 24

0.40 g (1.0 mmol) of perylene-3,4,9,10-tetracarboxylic-3,4-monoanhydride monopotassium salt and 0.50 g (4.9 mmol) of neopentanediamine are left standing for 1 h under an argon atmosphere with 4 ml of dist. water at room temperature. The mixture is then refluxed for 3 h. After cooling, the reaction mixture is diluted with 25 ml of water. The batch is subjected to filtration (over a D4 frit coated with silica gel); the dark violet precipitate is discarded. 5 ml of conc. hydrochloric acid are added to the filtrate and the mixture is then heated to boiling. The reaction mixture is then cooled to room temperature. The violet product is collected via suction filtration and dried at 120° C. Yield: 0.39 g (85%) of 3,4-dihydro-6-oxo-2H,6H-peryleno[3',4',3,4,5]-pyrido[1,2-a]pyrimidine-11,12-dicarboxylic anhydride, m.p.: >320° C.—IR (KBr): $\nu$=3435 cm$^{-1}$ m, 3027 w, 2961 s, 1768 s, 1731 s, 1700 s, 1631 s, 1593 s, 1506 m, 1402 m, 1379 w, 1334 w, 1304 m, 1266 s, 1232 w, 1173 w, 1152 m, 1127 m, 1079 w, 1025 s, 856 w, 808 m, 759 w, 737 m.—UV/vis (CHCl$_3$): $\lambda_{max}$=474 nm, 502, 538.—Fluorescence (CHCl$_3$): $\lambda_{max}$=558 nm, 598, 650.

Example 25

The procedure of Example 24 is repeated using the following educts and amounts: 1.58 g (3.52 mmol) of perylene-3,4,9,10-tetracarboxylic-3,4-monoanhydride monopotassium salt and 1.06 g (17.6 mmol) of ethylenediamine: yield: 1.34 g (88%) of perylene anhydride ethylene amidine, m.p.: >320° C.

What is claimed is:

1. A hydrazamimide of the general formula I

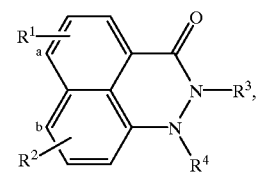

wherein R$^1$ and R$^2$ are each independently of the other (a) hydrogen or nitro, at least one of which radicals being nitro, or R$^1$ and R$^2$ together are (b) one of the following radicals

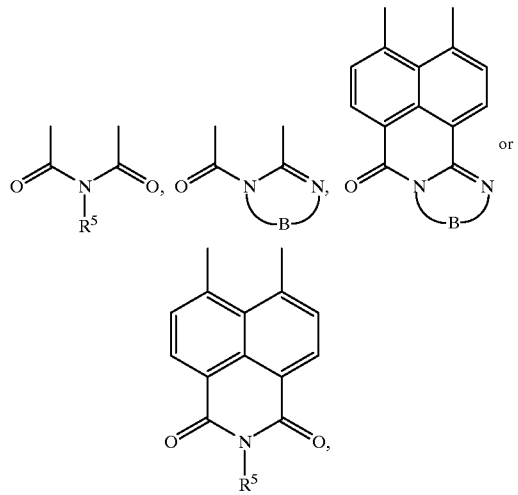

wherein B is

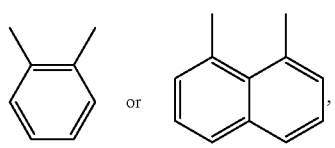

and R$^5$ is C$_1$–C$_{18}$alkyl or R$^3$ or R$^4$, in which case R$^1$ and R$^2$ are bound to the compound of formula I in the positions a and b, R$^3$ and R$^4$ are each independently of the other unbranched C$_1$–C$_{10}$alkyl.

2. A process for the preparation of a hydrazamimide I according to claim 1 by reacting the anhydride III

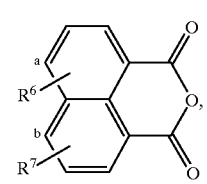

wherein $R^6$ and $R^7$ are each independently of the other (a) hydrogen or nitro, at least one of which radicals being nitro, or $R^6$ and $R^7$ together are (b)

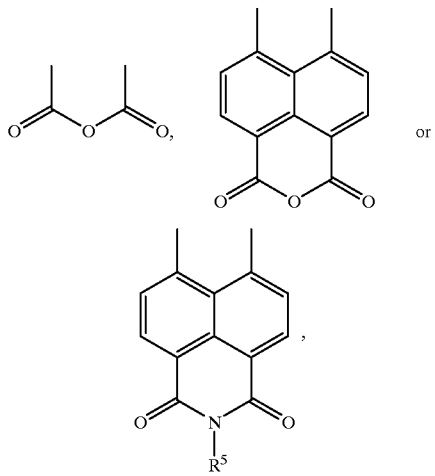

in which case $R^6$ and $R^7$ are bound to the compound of formula III in the positions a and b, with a disubstituted hydrazine, $R^3NHNHR^4$.

3. A process for the preparation of the hydrazamimide I according to claim 2, which comprises carrying out the reaction in the presence of a primary amine $R^5$ or of a diamine $H_2N$—B—$NH_2$, wherein B is

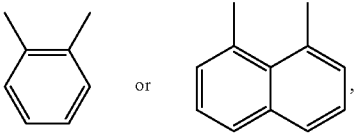

and $R^5$ is $C_1$–$C_{18}$alkyl or $R^3$ or $R^4$.

* * * * *